United States Patent
Takayama et al.

(10) Patent No.: US 6,175,118 B1
(45) Date of Patent: Jan. 16, 2001

(54) GAMMA CAMERA

(75) Inventors: Takuzo Takayama; Takashi Ichihara, both of Otawara; Nobutoku Motomura, Nasu-gun, all of (JP)

(73) Assignee: Kabushiki Kaisha Toshiba, Kawasaki (JP)

( * ) Notice: Under 35 U.S.C. 154(b), the term of this patent shall be extended for 0 days.

(21) Appl. No.: 09/119,624

(22) Filed: Jul. 21, 1998

(30) Foreign Application Priority Data

Jul. 23, 1997 (JP) .................................................... 9-197283

(51) Int. Cl.[7] .................................................. G01T 1/161
(52) U.S. Cl. ...................... 250/369; 250/363.07; 250/371
(58) Field of Search ......................... 250/363.07, 363.09, 250/369, 371, 252.1, 362

(56) References Cited

U.S. PATENT DOCUMENTS 5,371,672  12/1994  Motomura et al.
5,633,500 * 5/1997  Morgan et al. ................. 250/363.07

OTHER PUBLICATIONS

T. Takayama, et al. "Determination of Energy Window Width and Position For Scintigraphic Imaging Using Differnet Energy Resolution Detection With The Triple Energy Window (TEW) Scatter Compensation Method", IEEE 1998, Conference Record

* cited by examiner

Primary Examiner—Constantine Hannaher
Assistant Examiner—Albert Gagliardi
(74) Attorney, Agent, or Firm—Oblon, Spivak, McClelland, Maier & Neustadt, P.C.

(57) ABSTRACT

According to the present invention, sub-windows using a TEW technique are centered to energies corresponding to 1/n and 1/m of maximal photon number in a standard energy spectrum without any scattering component. It is thus possible to improve a count coefficiency, while broadening a main window to a maximal possible extent, without underestimating the scattering component and crosstalk component.

12 Claims, 4 Drawing Sheets

GAMMA CAMERA

BACKGROUND OF THE INVENTION

The present invention relates to a gamma camera for detecting a gamma ray radiated from radio-isotope (hereinafter referred to as RIs) administered to a human subject and imaging an internal concentration distribution of the RIs.

The gamma camera is classified into a type of imaging using a single photon nuclide emitting one photon at a decay of the RIs and a type of imaging using a positron nuclide emitting a pair of photons in opposite directions at a quenching of a positron. Recently, the imaging method has been diversified to cover the following methods.

(Static Imaging)

The imaging method is to obtain RIs distribution (plane image) by detecting photons, in a predetermined time period, with a single camera head fixed to a human subject and counting them.

(SPECT Imaging)

This imaging method comprises rotating one camera head around the human subject, while repeating the detection and counting of photons, and reconstructing RIs distribution (cross-sectional image), as in a CT scanning, on the basis of a count value obtained.

(Two Camera Heads-Opposed SPECT Imaging)

This imaging method comprises rotating two camera heads oppositely arranged with a human subject located therebetween while maintaining this positional relation, detecting/counting photons during this time period, and reconstructing a cross-sectional image, as in a CT scanning, on the basis of a count value obtained.

(Two Camera Head 90° Displaced SPECT Imaging)

This imaging method comprises rotating two camera head 90° displaced around a rotation axis while maintaining this positional relation, repeating the detection and counting of photons during this time period, and reconstructing a cross-sectional image, as in a CT scanning, on the basis of a count value obtained.

(Three Camera Head SPECT Imaging)

This imaging method comprises arranging three camera heads in a triangular array, rotating these cameras around a human subject while rotating these cameras while maintaining this positional relation, repeating the detection and counting of photons during this time period, and reconstructing a cross-sectional image, as in a CT scanning, on the basis of a count value obtained.

In these various imaging methods, in order to improve the image quality and quantitative property, various corrections are required, such as an energy correction, a linear correction for correcting a deformation in a marginal edge of a visual field, a uniformity correction for uniforming a variation in sensitivity of a photomultiplier, a scattering ray correction for eliminating scattering components, a crosstalk correction for correcting a crosstalk between two kinds of RIs differing in their photoelectric peaks, an absorption correction for correcting a count error resulting from the non-uniform coefficient of a living body, and so on.

A triple energy window (TEW) method is an excellent correction technique effective to not only the scattering correction but also a crosstalk correction. The TEW method requires three energy windows. The three energy window comprises, as shown in FIG. 1, one main window and two sub-windows. The main window has its center arranged at a photoelectric peak (Epeak) of a target nuclide. The two sub-windows are arranged one at each near side of the main window.

A scattering component (cross-hatched section) mixing into the main window is estimated by a trapezium approximation calculation from a calculated value of the two sub-windows. The estimated scattering component is subtracted from the calculated value of the main window. From the RIs it is possible to obtain the number of primary photons involved.

The greater the width of the main window, an image can be formed with many more photons. If the width of the main window is too greater, an amount of scattering lines mixed becomes greater, thus resulting in a lowering in an S/N ratio. It has been conventional practice to set the width of the main window to be 20% of the photoelectric peak Epeak corresponding to a maximum frequency or that of the sub-window to be 7% of the photoelectric peak Epeak, not depending upon the nuclide involved.

In the conventional method by which the window width is uniformly set in this way, there is a tendency that the width becomes too narrow at a relatively low photoelectric peak, for example, TI-201. This has been thus far indicated, but the setting method for optimizing these windows for respective nuclides has not yet currently established.

In order to make the above-mentioned absorption correction, it is necessary that the spatial distribution of an absorption coefficient on the human subject be measured with the use of an external ray source of a spatially uniform photon radiation frequency. The spatial distribution of the absorption coefficient can be found as follows. That is, the photons radiated from the external ray source are detected with a camera head after they have been transmitted through the human subject. The counting of only the photons whose energies are in the windows is made for respective incident positions and this is continued for a predetermined time period. The number of photons emitted for this time period from the external ray source is known and, being given as "$I_0$", then a relation below is established:

$$I_1 = I_0 \cdot e^{-\mu \cdot d}$$

where $I_1$: the number of photons transmitted through the human being, that is, a count value;

$\mu$: the absorption efficient; and d: the thickness of the human subject.

From this relation it is possible to find the absorption coefficient $\mu$.

By correcting a count value of the photons from the RIs, administered into the human subject, on the basis of the absorption coefficient it is possible to compensate for a count error resulting from a difference of the absorption coefficient.

In order to correct the scattering ray, the TEW method has been used even in finding a spatial distribution of the absorption coefficient. Since, however, the window is not optimized as set out above, there is a strong tendency that, in this case, the scattering ray is principally underestimated, thus presenting the problem of the absorption coefficient being lower than in an actual instance.

BRIEF SUMMARY OF THE INVENTION

It is accordingly an object of the present invention to achieve the optimization of a main window and sub-windows in the TEW technique effective to scattering and crosstalk corrections.

According to the present invention, the sub-windows using a TEW technique are centered to energies corresponding to 1/n and 1/m of maximal photon numbers in a standard energy spectrum without any scattering component. It is, thus, possible to improve a counting efficiency, while broadening a main window to a maximal possible extent, without underestimating scattering and crosstalk components.

According to the present invention, the low side sub-window using the TEW technique has its center arranged in a range between a photoelectric peak inherent in the nuclides of RIs and external ray source and a peak of a scattering ray associated with this photoelectric peak. It is possible to, while broadening the main window to a maximal possible extent, improve a counting efficiency without underestimating any scattering and crosstalk components.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Figure 1:
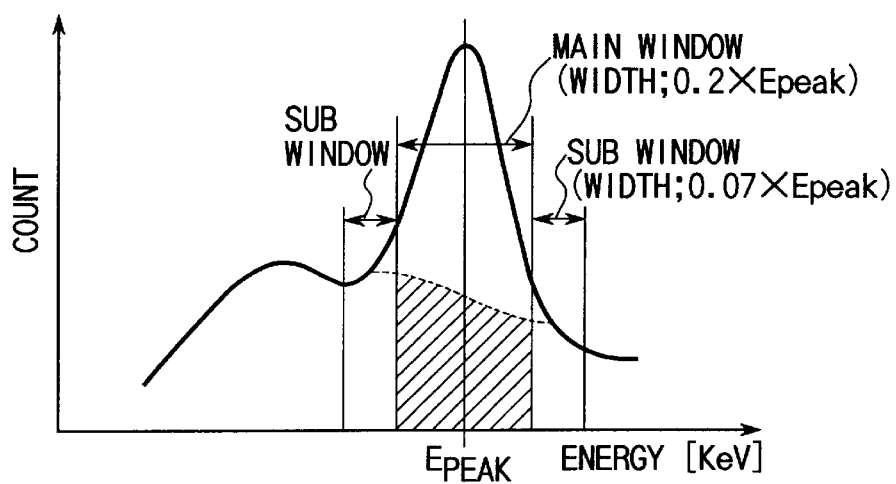
FIG. 1 is a view showing windows set by a conventional method.
Figure 3:
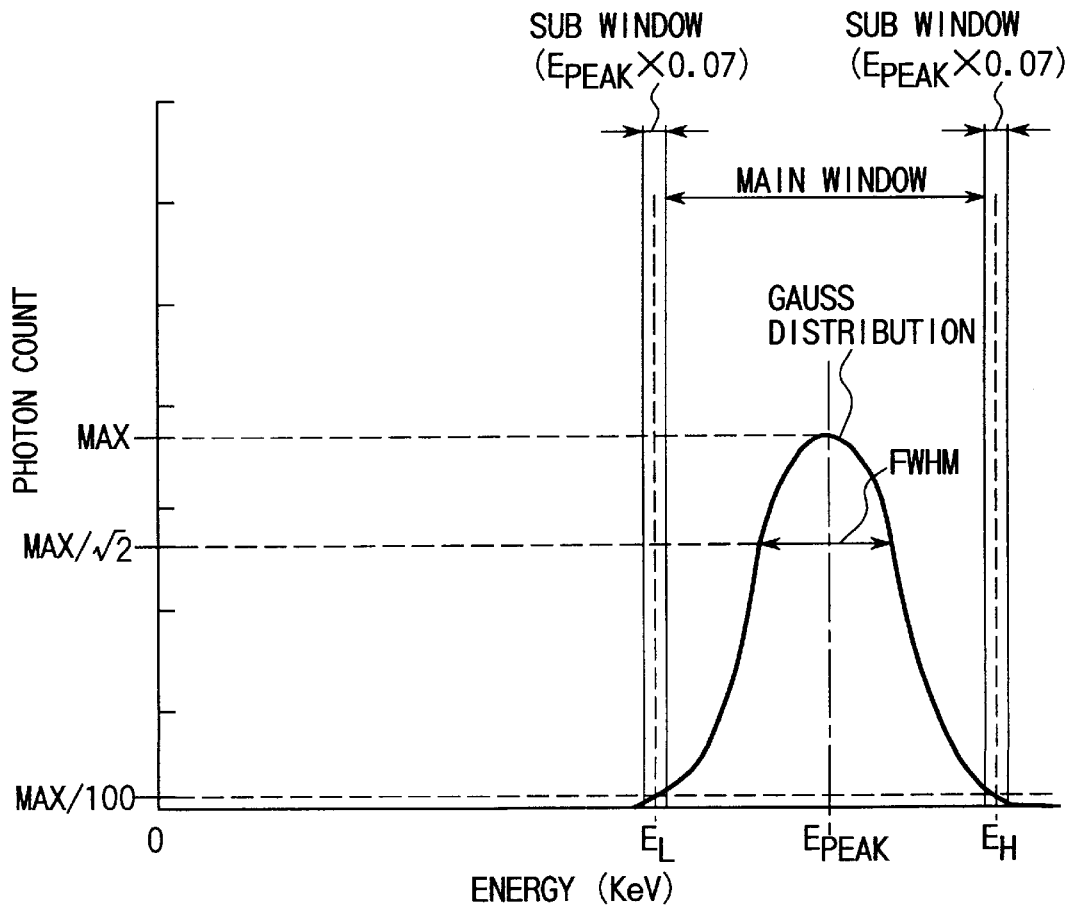
FIG. 3 is an explanatory view for explaining a main window, high side window and low side window set by a window controller in FIG. 2.

A gamma camera according to preferred embodiments of the present invention will be explained in more detail below with reference with the drawing. In this connection, the gamma camera is known, one type being a type of imaging using a single photon nuclide emitting a single photon at the decay of the RIs and another type being a type of imaging using a positron nuclide emitting a pair of photons in opposite directions at the decay of a positron. Here, the former type is an ordinary one. Further, the method of imaging includes the static imaging, the SPECT imaging, the two camera head opposed SPECT imaging, the two camera head 90°-displaced SPECT imaging, three camera head SPECT imaging, and so on. Here, the static imaging will be explained by way of example.

(First Embodiment)

Figure 2:
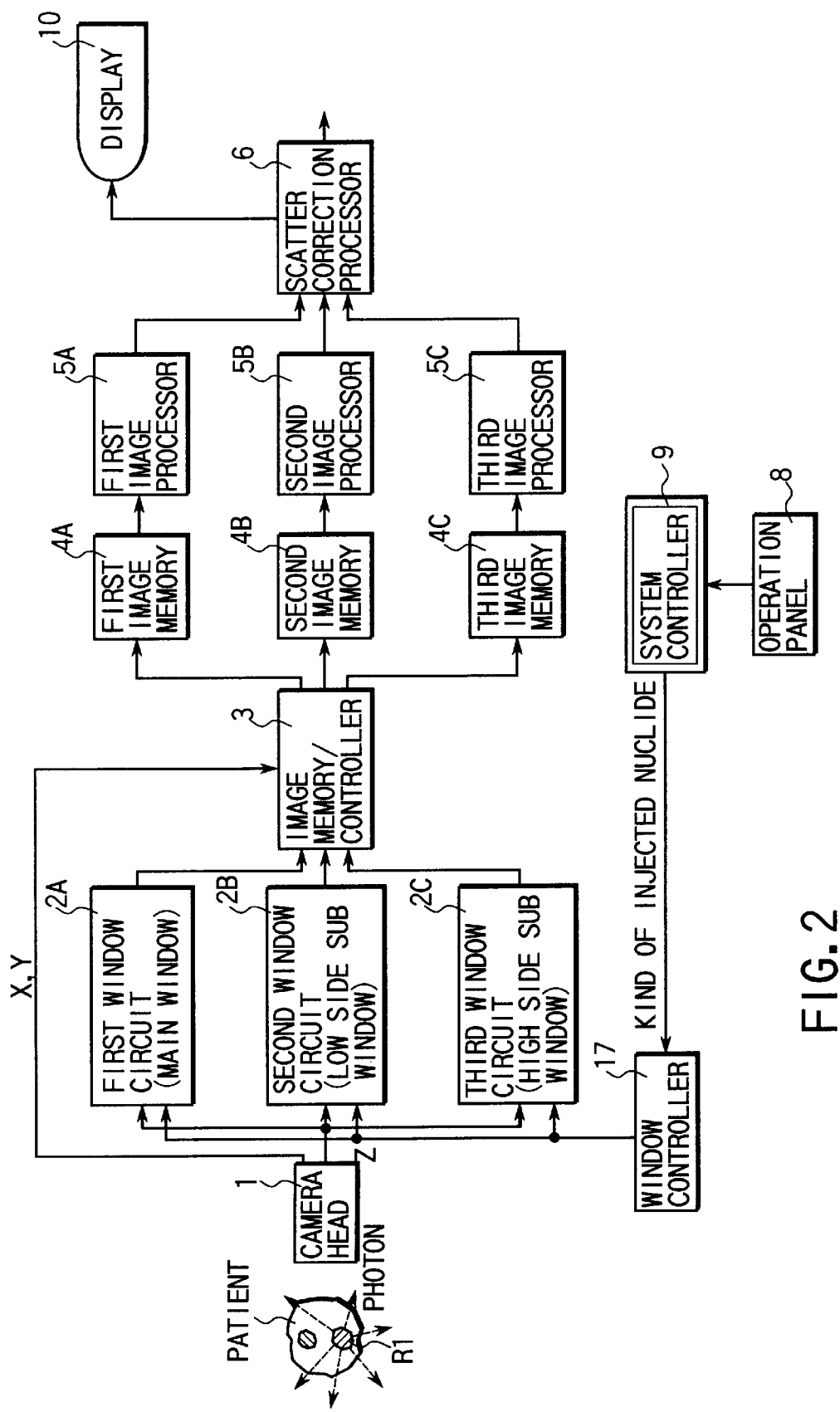
FIG. 2 is a block diagram showing an arrangement of a major section of a gamma camera according to a first embodiment of the present invention.

FIG. 2 is a block diagram showing an arrangement of a gamma camera according to a first embodiment of the present invention. A radio-isotope (RIs) administered to a human subject emits a gamma ray (photon) intermittently. A camera head 1 detects the photon and outputs an XY signal representing its incident position and a Z signal representing an energy of the photon. The camera head is, for example, two types, one being an Anger type equipped with the existing photomultiplier (PMT) and another type being a currently popular semiconductor array type. In the present invention, either type may be used. The Anger type has a camera head equipped with a collimator for restricting the incident direction of the photon, a scintillator for producing scintillations of light by the photons passed through the collimator, and a plurality of photomultipliers for converting the scintillation light to an electric signal. The semiconductor array type is such that, behind the collimator, a plurality of semiconductor elements, such as CdTe and CdZnTe, are arranged in a two-dimensional array to convert the photons to an electric signal.

The gamma camera of the present invention uses a TEW (triple energy window) technique to effect scattering correction and crosstalk correction. The TEW requires not-overlapped three energy windows.

The three energy windows comprise one main window and two sub-windows. The main window is centered at a photoelectric peak inherent in a target nuclide and two windows are arranged one adjacent the sub-window. It is to be noted that the sub-window defined adjacent the main window at a low side is referred to as a "low side sub-window" and the sub-window at a high side as a "high side sub-window". The scattering and crosstalk components mixed into the main windows are estimated, by a trapezium approximation calculation, based on the number of photons passed through the two sub-windows. The number of scattering components, etc., thus estimated is subtracted from the number of the photons passed through the main window. By doing so, it is possible to obtain the number of primary photons with the scattering and crosstalk components corrected.

In order to realize the TEW in a hardwarewise, three window circuits 2A, 2B and 2C are provided. First, the first window circuit 2A produces one pulse when an energy representing a Z signal from the camera head 1 enters the main window and the second window circuit 2B produces one pulse when an energy representing a Z signal enters the low side sub-window. And the third window circuit 2C produces one pulse when an energy representing a Z signal enters the high side sub-window.

Image memories 4A, 4B and 4C correspond to the window circuits 2A, 2B and 2C, respectively. Upon receipt of one pulse from any of the window circuits 2A, 2B and 2C, an image memory controller 3 delivers a control signal to the corresponding image memories 4A, 4B and 4C, the control signal incrementing a value of an address, by one, corresponding to the incident position in the corresponding image memories 4A, 4B and 4C. This action is continued for a predetermined time period. By doing so, the number of photons passed through the main window is counted at each incident position and stored in the image memory 4A. Similarly, the number of photons passing through the low side sub-window is counted at each incident position and stored in the image memory 4B. And the number of photons passed through the high side sub-window is counted and stored in the image memory 4C.

It is to be noted that data stored in the image memory 4A represents the concentration distribution (planar image) of RIs releasing main window-passed photons, referred to as "main image data" for convenience sake, and, similarly, data stored in the image memories 4B and 4C as "low side image data" and "high side image data", respectively.

Image processors 5A, 5B and 5C correct the image data stored in the image memories 4A, 4B and 4C, respectively. The correction includes the energy correction, the linear correction for correcting a distortion at the marginal edge of a visual field, and the correction for uniforming a variation in sensitivity of the photomultiplier and semiconductor device.

A scattering correction processor 6 performs the scattering correction of, in accordance with the TEW technique, eliminating scattering components which are mixed in the main image data on the basis of the low side image data and high side image data. The display 10 displays scattering-corrected main image data.

An operation panel 8 is provided for inputting the information relating to the nuclide administered to the human subject to a system controller 9. The system controller 9 transfers the information relating to the nuclide administered to the human subject to the window controller 7. The window controller 7 adjusts the energy windows (main window, low side sub-window and high side sub-window) of the above-mentioned window circuits 2A, 2B and 2C in accordance with the nuclide administered to the human subject. The window controller 7 stores, associated with the nuclide information, the information relating to the center energy and energy width of the respective window necessary to the setting of the respective energy windows of the window circuits 2A, 2B and 2C.

The present invention is directed to optimizing the center position and width of the three energy windows in accordance with the nuclide. The optimized three energy windows are determined as will be explained below.

As the RIs administered to the human subject, there are various nuclides such as Tc-99m and Tl-201. These nuclides are selected in accordance with the diagnostic object. As well-known, the energy corresponding to the maximal photon number, that is, the photoelectric peak, is inherent in the nuclide. The energy is, for example, 140 keV for the Tc-99m and 71 keV for the Tl-201. The energy resolution is determined depending upon the energy resolution inherent in the apparatus and photoelectric peak. The energy resolution is determined as a difference of an energy in a pair corresponding to the photon number of 2½ times the maximum photon number, that is, as the half width (FWHM). The photoelectric peak and energy resolution are determined depending upon the nuclide.

The inventors have determined the optimal three energy windows in accordance with the energy distribution (standard energy spectrum) of the photon number relating to a direct ray free from any scattering ray, that is, a ray directly incident to the camera head 1 from the RIs. First, the inventors approximate the standard energy spectrum to the Gaussian distribution (normal distribution) unconditionally determined from the photoelectric peak "Epeak" and energy resolution "FWHM".

The high side sub-window is centered on an energy $E_H$ corresponding to the photon number of 1/m times the maximum photon number "MAX" corresponding to the photoelectric peak on the standard energy spectrum. For the Anger type of camera head 1, the high side sub-window is determined to be a width of 0.07 times the photoelectric peak "Epeak" and, for the semiconductor type of camera head 1, to be a width of 0.03 times the photoelectric peak "Epeak".

Further, the low side sub-window is centered on the energy $E_L$ corresponding to the photon number of 1/n times the maximum photon number "MAX" corresponding to the photoelectric peak on the standard energy spectrum. Like the high side sub-window $E_L$, the low side sub-window is determined to be a width of 0.07 times of the photoelectric peak "Epeak" for the Anger type of camera head 1 and to be a width of 0.03 times of the photoelectric peak "Epeak" for the semiconductor type of camera head 1.

The main window is determined between the low side sub-window and the high side sub-window. That is, the main window is determined in a range from the maximum energy of the low side sub-window to the minimum energy of the high side sub-window.

The "m" and "n" represent a rational number exceeding 1. In the experiment conducted by the inventors, m=n=100 at which the most optimal window is designed. It is to be noted that, if m=n=100±10% (90–100), the optimization falls in an allowable range.

Figure 4:
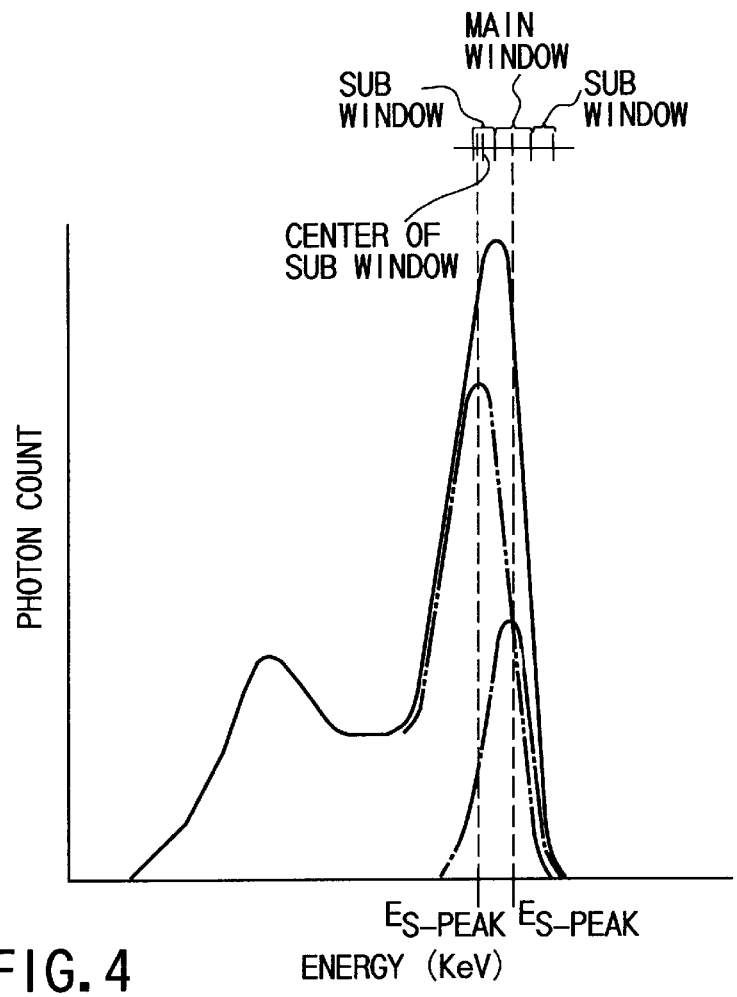
FIG. 4 is a view showing an optimal position of the low side sub-window.

The number "m" may be adjusted in accordance with the energy (scattering peak) at which the photon number of the scattering ray is maximal. The scattering peak is associated with the photoelectric peak and can be measured with the use of a phantom. As shown in FIG. 4, an amount of scattering ray mixed into the main window can be reduced by adjusting the "m" so as to have the center energy of the low side sub-window set at a position between the photoelectric peak $E_{p\text{-}peak}$ and the scattering peak $E_{s\text{-}peak}$.

For the Tc-99m, for example, the photoelectric peak is 140 keV and the energy resolution is 16.5 keV. If, in this case, the width of the sub-window is set to 7% of the photoelectric peak, the low side sub-window is set to 116.2 keV to 126.0 keV, the high side sub-window is set to 154.0 keV to 163.8 keV and the main window is set to 126.0 keV to 154.0 keV. At this time, the energy width of the main window becomes about 20.0% of the photoelectric peak.

For the Tl-201, the photoelectric peak is 74 keV and the energy resolution is 12.6 keV. Even in this case, if the width of the sub-window is set to 7% of the photoelectric peak, the low side sub-window is 51.3 keV to 56.5 keV, the high side sub-window is 91.5 keV to 96.7 keV and the main window is 56.5 keV to 91.5 keV. And the energy width becomes about 47.3% of the photoelectric peak.

If, in this example, the center of the low side sub-window becomes 53.9 keV and that of the high side sub-window becomes 94.1 keV, then it is possible, according to the present invention, to obtain substantially the same effect if the center of the low side sub-window is located in a range from 51 keV to 56 keV and the center of the high side window is located in a range from 92 keV to 97 keV.

The main window and sub-window determined in accordance with the photoelectric peak of the nuclide and energy window have their scattering components not underestimated. And it is possible to improve the counting efficiency, by making the main window as wide as possible, and to optimize the energy window.

(Second Embodiment)

Figure 5:
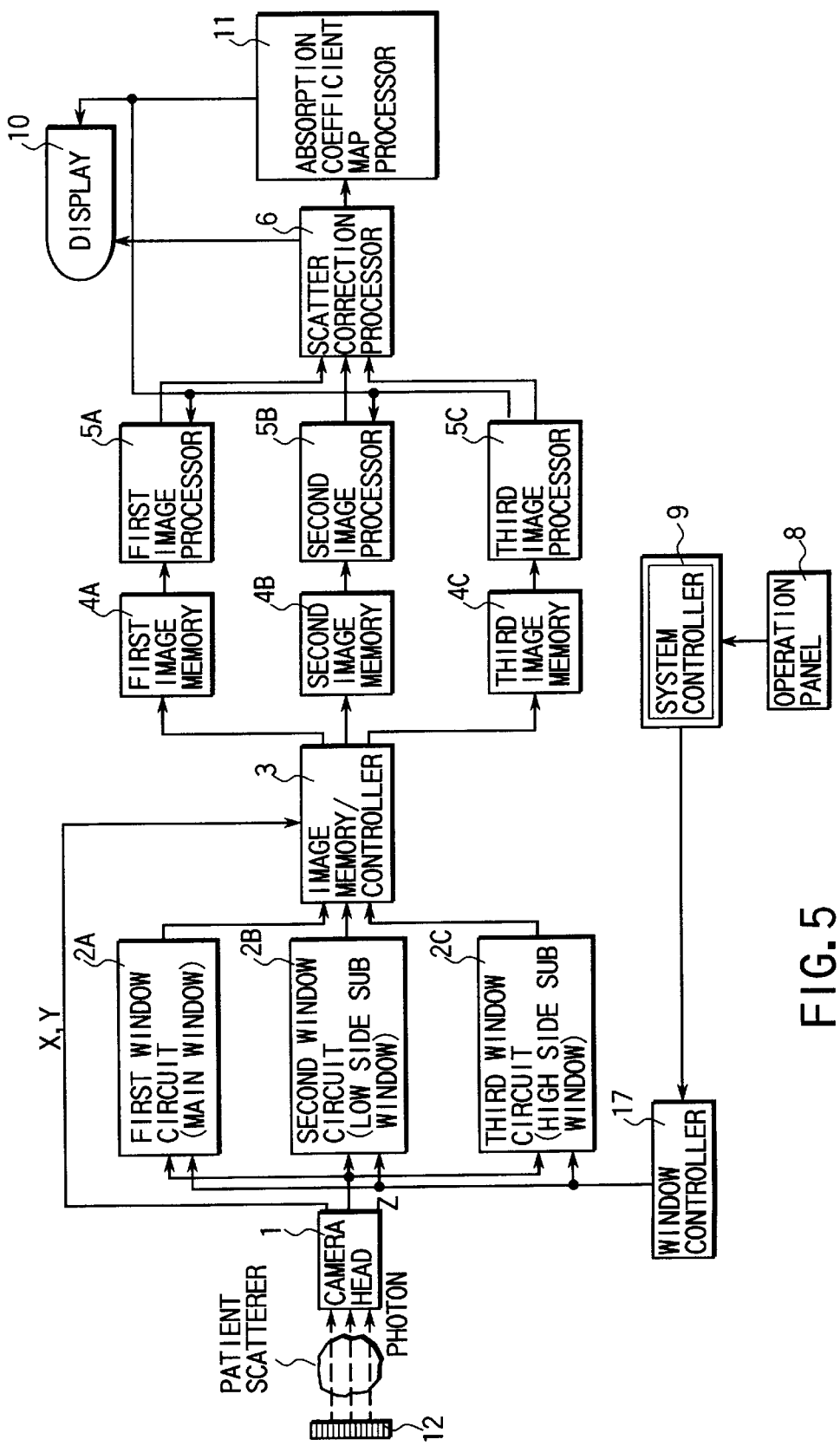
FIG. 5 is a block diagram showing an arrangement of a major section of a gamma camera according to a second embodiment of the present invention.

FIG. 5 shows an arrangement of a gamma camera according to a second embodiment. In FIG. 5, the same reference numerals are employed to designate parts or elements corresponding to those shown in FIG. 2 and any further explanation is, therefore, omitted. The gamma camera of this embodiment operates in two operation modes. The first mode is for an operation for creating an absorption coefficient map relation to an external ray source. The second mode is a mode effected subsequent to the first mode and is for an operation for subjecting the number of photons which come from RIs administered to the human subject to absorption correction with the use to an absorption coefficient map created at the first mode and for obtaining the concentration distribution (planar image, SPECT image, PET image) from a result of correction.

The optimization of the window of the first embodiment can also be applied to the creation of an absorption coefficient map in the first mode of the present embodiment. In the first mode, a plane-like external ray source 12 whose photon radiation rate is spatially uniform is arranged in a position opposite to the camera head 1 with the human subject therebetween. The photons radiated from the external ray source 12 and passed through the human subject 12 are counted for a predetermined period through a camera head 1. The number of photons radiated from the external ray source 12 during this period is already known and, with this number given by "$I_0$", the following relation is established:

$$I_1 = I_0 \cdot e^{-\mu \cdot d}$$

where $I_1$: the number of photons passed through the human subject;

$\mu$: the absorption efficient; and d: the thickness of the human subject.

From this relation it is possible to find the absorption coefficient "$\mu$", by an absorption coefficient map processor 11, from this relation. In order to improve the precision of the absorption coefficient, it is effective to eliminate scattering components, with high precision, by the TEW technique. For the first mode, the data held in the image memory 4A represents a spatial distribution corresponding to the number of photons radiated from the ray source, passed through the human subject and passed through the main window, and is referred to as main transmission image data for convenience sake. The data retained in the image memories 4B and 4C are referred to, similarly, as the row side transmission image data and high side transmission image data, respectively.

In accordance with the TEW technique, the collected main transmission image data is corrected by scatter coefficient processor 6 on the basis of the low side transmission image data and high side transmission image data. The absorption coefficient map is created under the absorption coefficient map processor 11 on the basis of the amended main transmission image data.

In the case where the absorption coefficient map is created with the use of such external ray source 12, it is possible to, by optimizing the three windows in accordance with the nuclide as set out above, improve the counting efficiency while broadening the main window to a maximal possible extent and do this without underestimating any scattering component. By doing so it is possible to generate the absorption coefficient map with high precision.

(Third Embodiment)

Figure 6:
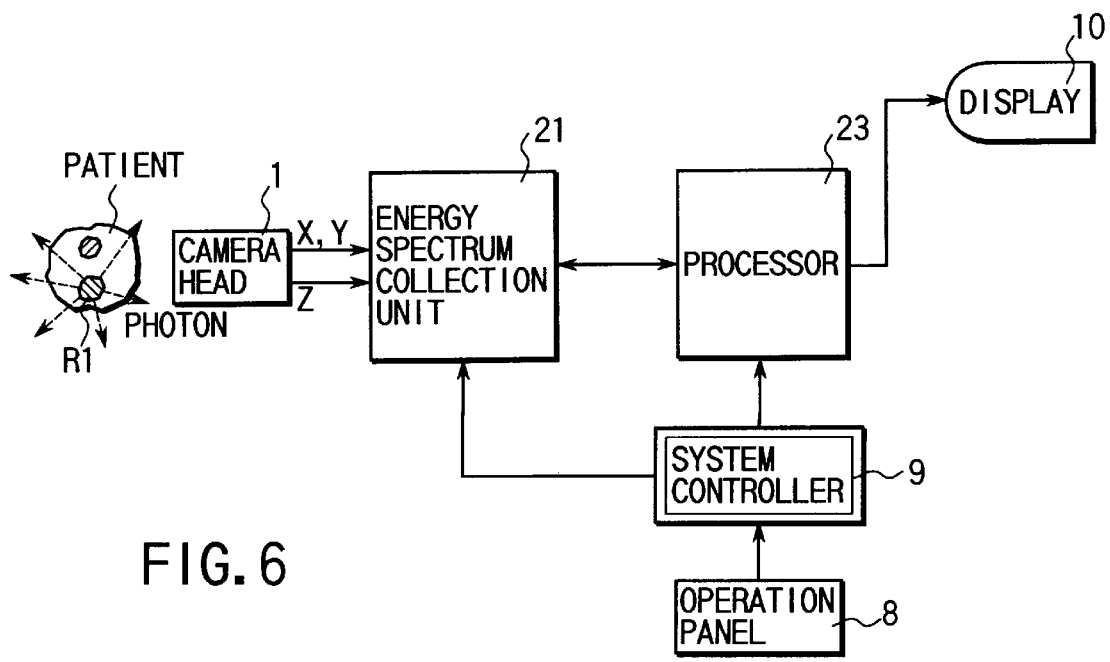
FIG. 6 is a block diagram showing an arrangement of a major section of a gamma camera according to a third embodiment of the present invention.

FIG. 6 shows an arrangement of a major section of a gamma camera according to a third embodiment of this invention. For the first and second embodiments, the TEW technique is realized in the hardware fashion by providing the window circuits 2A, 2B, 2C, etc., while, for the third embodiment, it is realizing, in a software function, under a computer-readable/computer-executable program stored in a storage medium, such as a magnetic disk.

An energy spectrum collection unit 21 collects an energy spectrum at each incident position on the basis of an output of the camera head (camera body). The energy spectrum is obtained by collecting count values on a plurality of very small windows of narrow width continuously arranged at different energy values. A processor 23 executes a program code. As in the first embodiment, the program code has means for determining the widths and positions of a main window, low side window, high side window in accordance with the kind of input nuclide, means for counting the number of photons corresponding to the main window, low side window and high side window by adding together collected count values of the very small windows in the energy spectrum, and means for making the calculation of eliminating scattering rays by the TEW technique from the number of photons counted.

In this way, the present invention can also be applied to the case of implementing the TEW technique with the use of the program code.

The present invention is not restricted to the above-mentioned embodiments and various changes or modifications of the present invention can be made without departing from the spirit and scope of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A gamma camera comprising:

a camera head for detecting photons radiated from RIs administered to a human subject or from an external ray source;

means for counting, out of the detected photons, those photons whose energy enters within a main window, the counted photon number being given as a first value;

means for counting, out of the detected photons, those photons whose energy enters within a first sub-window arranged to a high energy side relative to the main window, the counted photon number being given as a second value, the first sub-window being centered to an energy corresponding to the number of photons of MAX/n in a standard energy spectrum where n represents a rational number exceeding one, the standard energy spectrum represents an energy distribution of the photon number relating to direct rays from the RIs without scattering rays, and MAX represents a maximal photon number of the standard energy spectrum;

means for counting, out of the detected photons, those photons whose energy enters within a second sub-window arranged to a low energy side relative to the main window, the counted photon number being given as a third value, the second sub-window being centered to an energy corresponding to the photon number of MAX/m in the standard energy spectrum where m represents a rational number exceeding one, and means for correcting the first value on the basis of the second and third values.

2. A gamma camera apparatus according to claim 1, wherein the n and m are selected from a 100±10% range.

3. A gamma camera apparatus according to claim 1, wherein the n is set to be equal in value to the m.

4. A gamma camera apparatus according to claim 1, wherein the standard energy spectrum is approximated to a Gaussian distribution specified from a photoelectric peak inherent in the RIs and an energy resolution inherent in the camera head.

5. A gamma camera apparatus according to claim 1, further comprising means for reconstructing a concentration distribution of the RIs or an absorption coefficient map of the human subject.

6. A gamma camera apparatus according to claim 1, wherein the first sub-window is set to a width of a % of a photoelectric peak inherent in the RIs, the second sub-window is set to a width of b % of the photoelectric peak, and the main window is set to be present between the set first sub-window and the set second sub-window.

7. A gamma camera comprising:
  a camera head for detecting photons radiated from RIs administered to a human subject or from an external ray source;
  means for counting, out of the detected photons, those photons whose energy enters within a main window, the counted photon number being given as a first value;
  means for counting, out of the detected photons, those photons at each incident position whose energy enters within a first sub-window arranged to a high energy side relative to the main window, the counted photon number being given as a second value;
  means for counting, out of the detected photons, those photons at each incident position whose energy enters within a second sub-window arranged to a low energy side relative to the main window, the center of the second sub-window being arranged between a photoelectric peak inherent in the RIs and a peak of a scattering ray associated with the photoelectric peak, the counted photon number being given as a third value; and
  means for correcting the first value on the basis of the second and third values.

8. A gamma camera apparatus according to claim 7, wherein, when a nuclide of the administered RIs or the external ray source is Ti-201, the center of the second sub-window is arranged in a 51 to 56 KeV range.

9. A gamma camera apparatus according to claim 7, wherein the second sub-window is set to a width of a % of a photoelectric peak inherent in the RIs, the main window is set to be width of b % of the photoelectric peak arranged to the set second sub-window and the first sub-window is set to be a width of c % of the photoelectric peak arranged to the set main window.

10. A gamma camera comprising:
  a camera head for detecting photons radiated from RIs administered to a human subject or from an external ray source;
  means for counting, out of the detected photons, those photons whose energy enters within a main window, the photon number being given as a first value,
  means for counting, out of the detected photons, those photons whose energy enters within a first sub-window arranged to a high energy side relative to the main window, the photon number being given as a second value;
  means for counting, out of the detected photons, those photons whose energy enters within a second sub-window arranged to a low energy side relative to the main window, the photon number being given as a third value;
  means for correcting the first value on the basis of the second and third values; and
  means for adjusting the main window, first sub-window and second sub-window in accordance with a nuclide of the RIs or external ray source, the first sub-window being centered to an energy corresponding to the photon number of MAX/n in a standard energy spectrum, and the second sub-window being centered to an energy corresponding to the photon number of MAX/m in the standard energy spectrum, where
    the n and m represent a rational number exceeding one;
    the standard energy spectrum represents an energy distribution of the photon number relating to direct rays from the RIs; and
    the MAX represents a maximum photon number in the standard energy spectrum.

11. A data processing method for correcting data acquired by a gamma camera, out of photons radiated from RIs administered to a human subject or from an external ray source, the number of photons whose energy enters a main window being corrected on the basis of the number of photons whose energy enters a first sub-window arranged to a high energy side relative to the main window and the number of photons whose energy enters the second sub-window arranged to a low energy side relative to the main window, the correcting method comprising the steps of:
  centering the first sub-window to an energy corresponding to the number of photons of MAX/n in a standard energy spectrum, and
  centering the second window to an energy corresponding to the number of photons of MAX/m in a standard energy spectrum,
  the n and m represent a rational number exceeding a unity;
  the standard energy spectrum represents an energy distribution of the photon number relating to direct rays from the RIs without any scattering ray; and
  the MAX represents a maximum photon number of the standard energy spectrum.

12. A data processing method for correcting data acquired by a gamma camera, out of photons radiated from RIs administered to a human being or from an external ray source, the number of photons whose energy enters a main window being corrected on the basis of the number of photons whose energy enters a first sub-window arranged to a high energy side relative to the main window and the number of photons whose energy enters a second sub-window arranged to a low energy side relative to the main window, the correcting method comprising arranging a center of the second sub-window in a range between a photoelectric peak inherent in the RIs and a peak of a scattering ray associated with the photoelectric peak.

* * * * *